(12) United States Patent
Coelingh Bennink et al.

(10) Patent No.: US 7,968,514 B2
(45) Date of Patent: Jun. 28, 2011

(54) PHARMACEUTICAL COMPOSITION FOR TREATING OR PREVENTING OVARIAN CANCER

(75) Inventors: Herman Jan Tijmen Coelingh Bennink, Werkhoven (NL); Monique Visser, HT Zeist (NL)

(73) Assignee: Pantarhei Bioscience B.V., Zeist (NL)

( * ) Notice: Subject to any disclaimer, the term of this patent is extended or adjusted under 35 U.S.C. 154(b) by 68 days.

(21) Appl. No.: 12/093,908

(22) PCT Filed: Nov. 16, 2006

(86) PCT No.: PCT/NL2006/050289
§ 371 (c)(1),
(2), (4) Date: May 15, 2008

(87) PCT Pub. No.: WO2007/058536
PCT Pub. Date: May 24, 2007

(65) Prior Publication Data
US 2009/0060931 A1 Mar. 5, 2009

Related U.S. Application Data

(60) Provisional application No. 60/736,877, filed on Nov. 16, 2005.

(30) Foreign Application Priority Data

Nov. 16, 2005 (EP) .................................. 05110819

(51) Int. Cl.
*A61K 38/18* (2006.01)
*C07K 14/49* (2006.01)
*C07K 14/48* (2006.01)
*C07K 1/00* (2006.01)
*C07K 14/00* (2006.01)
*C07K 17/00* (2006.01)

(52) U.S. Cl. .......................................... 514/8; 530/395

(58) Field of Classification Search .................. None
See application file for complete search history.

(56) References Cited

U.S. PATENT DOCUMENTS 5,840,839 A * 11/1998 Wang et al. .................... 530/325
6,455,041 B1 9/2002 Dunbar
6,455,941 B1 9/2002 Lee et al.

FOREIGN PATENT DOCUMENTS

| WO | 94/22472 A1 | 10/1994 |
| WO | 99/42581 A1 | 8/1999 |
| WO | 01/02000 A2 | 1/2001 |
| WO | 2005/026735 A2 | 3/2005 |

OTHER PUBLICATIONS

Choudhury et al., Journal of Reproductive Immunology, Jan. 2009, vol. 79, pp. 137-147.*
Sherman, LA et al, 1998, Critical reviews in Immunol, 18(1-2): 47-54.*
Lauritzsen et al (International Journal of Cancer, 1998, vol. 78, pp. 216-222).*
Sarma et al (Journal of Experimental Medicine, 1999, vol. 189, pp. 811-820).*
Riott et al (Immunology, Fourth Edition, 1996, Mosby, p. 7.9-7.11).*
XP-002368728. WPI, Derwent Publications Ltd., 1995.
Japanese Patent Abstract JP1993-0249404 XP-002368728. WPI, Derwent Publications Ltd., 1995.
Paterson M, Aitken RJ. Development of vaccines targeting the zona pellucida. Curr Opin Immunol 1989-1990, 2:743-7.
Gupta SK, Srivastava N, Choudhury S, Rath A, Sivapurapu N, Gahlay GK, Batra D. Update on zona pellucida glycoproteins based contraceptive vaccine. J Reprod Immunol 2004, 62:79-89.
Zhang X, Lou YH, Koopman M, Doggett T, Tung KS, Curtiss R 3rd. Antibody responses and infertility in mice following oral immunization with attenuated *Salmonella typhimurium* expressing recombinant murine ZP3. Biol Reprod 1997 56:33-41.
Naz RK, Gupta SK, Gupta JC, Vyas HK, Talwar GP. Recent advances in contraceptive vaccine development: a mini review. Hum Reprod 2005, 20:3271-83.
Chamberlin ME, Dean J. Human homolog of the mouse sperm receptor. Proc Natl Acad Sci U S A. 1990, 87:6014-8.
Harris JD, Hibler DW, Fontenot GK, Hsu KT, Yurewicz EC, Sacco AG. Cloning and characterization of zona pellucida genes and cDNA from a variety of mammalian species. The ZPA, ZPB and ZPC gene families. DNA Sequence 1994, 4:363-393 (Abstract).
Kolluri SK, Kaul R, Banerjee K, Gupta SK. Nucleotide sequence of cDNA encoding bonnet monkey (Macaca radiata) zona pellucida glycoprotein-ZP3. Reprod Fertil Dev 1995, 7:1209-12 (Abstract).
Zhu X, Naz RK. Comparison of ZP3 protein sequences among vertebrate species: to obtain a consensus sequence for immunocontraception. Front Biosci 1999, 4:D212-5 (Abstract).
Harris JD, Seid CA, Fontenot GK, Liu HF. Expression and purification of recombinant human zona pellucida proteins. Protein Expr Purif 1999, 16:298-307.
Srivastava N, Santhanam R, Sheela P, Mukund S, Thakral SS, Malik BS, Gupta SK. Evaluation of the immunocontraceptive potential of *Escherichia coli*-expressed recombinant dog ZP2 and ZP3 in a homologous animal model. Reproduction 2002, 123:847-57.
Lloyd ML, Shellam GR, Papadimitriou JM, Lawson MA. Immunocontraception is induced in BALB/c mice inoculated with murine cytomegalovirus expressing mouse zona pellucida 3. Biol Reprod. 2003;68:2024-32.

(Continued)

*Primary Examiner* — Anne M. Gussow
(74) *Attorney, Agent, or Firm* — Browdy and Neimark, PLLC

(57) ABSTRACT

The invention relates to therapeutic and prophylactic treatment of ovarian cancer and metastases thereof. More specifically, the invention relates to immunogenic polypeptides comprising at least a portion of an ovarian tissue cell-associated protein or immunologically active variants thereof and to nucleic acids encoding such polypeptides and to the use thereof in immunotherapeutic methods of treatment. Said immunogenic polypeptides are provided by the zona pellucida (ZP) glycoproteins. ZP glycoproteins and fragments thereof that can induce a $CD8^+$ and/or $CD4^+$ T cell response as well as nucleic acid sequences encoding them can suitably be used in the present immunotherapeutic strategies.

11 Claims, No Drawings

OTHER PUBLICATIONS

Bagavant H, Thillai-Koothan P, Sharma MG, Talwar GP, Gupta SK. Antifertility effects of porcine zona pellucida-3 immunization using permissible adjuvants in female bonnet monkeys (*Macaca radiata*): reversibility, effect on follicular development and hormonal profiles. J Reprod Fertil 1994, 102:17-25.

Paterson M, Wilson MR, Morris KD, van Duin M, Aitken RJ. Evaluation of the contraceptive potential of recombinant human ZP3 and human ZP3 peptides in a primate model: their safety and efficacy. Am J Reprod Immunol 1998, 40:198-209 (Abstract).

Paterson M, Wilson MR, Jennings ZA, van Duin M, Aitken RJ. Design and evaluation of a ZP3 peptide vaccine in a homologous primate model. Mol Hum Reprod 1999, 5:342-52.

Paterson M, Jennings ZA, Wilson MR, Aitken RJ. The contraceptive potential of ZP3 and ZP3 peptides in a primate model. J Reprod Immunol 2002, 53:99-107.

Clydesdale G, Pekin J, Beaton S, Jackson RJ, Vignarajan S, Hardy CM. Contraception in mice immunized with recombinant zona pellucida subunit 3 proteins correlates with Th2 responses and the levels of interleukin 4 expressed by CD4+ cells. Reproduction 2004, 128:737 45.

Rhim SH, Millar SE, Robey F, Luo AM, Lou YH, Yule T, Allen P, Dean J, Tung KS. Autoimmune disease of the ovary induced by a ZP3 peptide from the mouse zona pellucida. J Clin Invest 1992, 89:28-35.

Lou Y, Tung KS. T cell peptide of a self-protein elicits autoantibody to the protein antigen. Implications for specificity and pathogenetic role of antibody in autoimmunity. J Immunol 1993, 151:5790-9.

Lou Y, Ang J, Thai H, McElveen F, Tung KS. A zona pellucida 3 peptide vaccine induces antibodies and reversible infertility without ovarian pathology. J Immunol 1995, 155:2715-20.

\* cited by examiner

SEQUENCE LISTING

```
<160> NUMBER OF SEQ ID NOS: 4

<210> SEQ ID NO 1
<211> LENGTH: 638
<212> TYPE: PRT
<213> ORGANISM: human
<220> FEATURE:
<223> OTHER INFORMATION: Zona pellucida protein ZP1

<400> SEQUENCE: 1

Met Ala Gly Gly Ser Ala Thr Thr Trp Gly Tyr Pro Val Ala Leu Leu
1               5                   10                  15

Leu Leu Val Ala Thr Leu Gly Leu Gly Arg Trp Leu Gln Pro Asp Pro
                20                  25                  30

Gly Leu Pro Gly Leu Arg His Ser Tyr Asp Cys Gly Ile Lys Gly Met
            35                  40                  45

Gln Leu Leu Val Phe Pro Arg Pro Gly Gln Thr Leu Arg Phe Lys Val
        50                  55                  60

Val Asp Glu Phe Gly Asn Arg Phe Asp Val Asn Asn Cys Ser Ile Cys
65                  70                  75                  80

Tyr His Trp Val Thr Ser Arg Pro Gln Glu Pro Ala Val Phe Ser Ala
                85                  90                  95

Asp Tyr Arg Gly Cys His Val Leu Glu Lys Asp Gly Arg Phe His Leu
            100                 105                 110
```

-continued

Arg Val Phe Met Glu Ala Val Leu Pro Asn Gly Arg Val Asp Val Ala
115                 120                 125

Gln Asp Ala Thr Leu Ile Cys Pro Lys Pro Asp Pro Ser Arg Thr Leu
130                 135                 140

Asp Ser Gln Leu Ala Pro Pro Ala Met Phe Ser Val Ser Thr Pro Gln
145                 150                 155                 160

Thr Leu Ser Phe Leu Pro Thr Ser Gly His Thr Ser Gln Gly Ser Gly
                165                 170                 175

His Ala Phe Pro Ser Pro Leu Asp Pro Gly His Ser Ser Val His Pro
            180                 185                 190

Thr Pro Ala Leu Pro Ser Pro Gly Pro Gly Pro Thr Leu Ala Thr Leu
        195                 200                 205

Ala Gln Pro His Trp Gly Thr Leu Glu His Trp Asp Val Asn Lys Arg
210                 215                 220

Asp Tyr Ile Gly Thr His Leu Ser Gln Glu Gln Cys Gln Val Ala Ser
225                 230                 235                 240

Gly His Leu Pro Cys Ile Val Arg Arg Thr Ser Lys Glu Ala Cys Gln
                245                 250                 255

Gln Ala Gly Cys Cys Tyr Asp Asn Thr Arg Glu Val Pro Cys Tyr Tyr
            260                 265                 270

Gly Asn Thr Ala Thr Val Gln Cys Phe Arg Asp Gly Tyr Phe Val Leu
        275                 280                 285

Val Val Ser Gln Glu Met Ala Leu Thr His Arg Ile Thr Leu Ala Asn
290                 295                 300

Ile His Leu Ala Tyr Ala Pro Thr Ser Cys Ser Pro Thr Gln His Thr
305                 310                 315                 320

Glu Ala Phe Val Val Phe Tyr Phe Pro Leu Thr His Cys Gly Thr Thr
                325                 330                 335

Met Gln Val Ala Gly Asp Gln Leu Ile Tyr Glu Asn Trp Leu Val Ser
            340                 345                 350

Gly Ile His Ile Gln Lys Gly Pro Gln Gly Ser Ile Thr Arg Asp Ser
        355                 360                 365

Thr Phe Gln Leu His Val Arg Cys Val Phe Asn Ala Ser Asp Phe Leu
370                 375                 380

Pro Ile Gln Ala Ser Ile Phe Pro Pro Ser Pro Ala Pro Met Thr
385                 390                 395                 400

Gln Pro Gly Pro Leu Arg Leu Glu Leu Arg Ile Ala Lys Asp Glu Thr
                405                 410                 415

Phe Ser Ser Tyr Tyr Gly Glu Asp Asp Tyr Pro Ile Val Arg Leu Leu
            420                 425                 430

Arg Glu Pro Val His Val Glu Val Arg Leu Leu Gln Arg Thr Asp Pro
        435                 440                 445

Asn Leu Val Leu Leu Leu His Gln Cys Trp Gly Ala Pro Ser Ala Asn
450                 455                 460

Pro Phe Gln Gln Pro Gln Trp Pro Ile Leu Ser Asp Gly Cys Pro Phe
465                 470                 475                 480

Lys Gly Asp Ser Tyr Arg Thr Gln Met Val Ala Leu Asp Gly Ala Thr
                485                 490                 495

Pro Phe Gln Ser His Tyr Gln Arg Phe Thr Val Ala Thr Phe Ala Leu
            500                 505                 510

Leu Asp Ser Gly Ser Gln Arg Ala Leu Arg Gly Leu Val Tyr Leu Phe
        515                 520                 525

Cys Ser Thr Ser Ala Cys His Thr Ser Gly Leu Glu Thr Cys Ser Thr
530                 535                 540

Ala Cys Ser Thr Gly Thr Thr Arg Gln Arg Arg Ser Ser Gly His Arg
545                 550                 555                 560

Asn Asp Thr Ala Arg Pro Gln Asp Ile Val Ser Ser Pro Gly Pro Val
                565                 570                 575

Gly Phe Glu Asp Ser Tyr Gly Gln Glu Pro Thr Leu Gly Pro Thr Asp
            580                 585                 590

Ser Asn Gly Asn Ser Ser Leu Arg Pro Leu Leu Trp Ala Val Leu Leu
        595                 600                 605

Leu Pro Ala Val Ala Leu Val Leu Gly Phe Gly Val Phe Val Gly Leu
    610                 615                 620

Ser Gln Thr Trp Ala Gln Lys Leu Trp Glu Ser Asn Arg Gln
625                 630                 635

<210> SEQ ID NO 2
<211> LENGTH: 745
<212> TYPE: PRT
<213> ORGANISM: human
<220> FEATURE:
<223> OTHER INFORMATION: Zona pellucida protein ZP2

<400> SEQUENCE: 2

Met Ala Cys Arg Gln Arg Gly Gly Ser Trp Ser Pro Ser Gly Trp Phe
1               5                   10                  15

Asn Ala Gly Trp Ser Thr Tyr Arg Ser Ile Ser Leu Phe Phe Ala Leu
            20                  25                  30

Val Thr Ser Gly Asn Ser Ile Asp Val Ser Gln Leu Val Asn Pro Ala
        35                  40                  45

Phe Pro Gly Thr Val Thr Cys Asp Glu Arg Glu Ile Thr Val Glu Phe
    50                  55                  60

Pro Ser Ser Pro Gly Thr Lys Lys Trp His Ala Ser Val Val Asp Pro
65                  70                  75                  80

Leu Gly Leu Asp Met Pro Asn Cys Thr Tyr Ile Leu Asp Pro Glu Lys
                85                  90                  95

Leu Thr Leu Arg Ala Thr Tyr Asp Asn Cys Thr Arg Arg Val His Gly
            100                 105                 110

Gly His Gln Met Thr Ile Arg Val Met Asn Asn Ser Ala Ala Leu Arg
        115                 120                 125

His Gly Ala Val Met Tyr Gln Phe Phe Cys Pro Ala Met Gln Val Glu
    130                 135                 140

Glu Thr Gln Gly Leu Ser Ala Ser Thr Ile Cys Gln Lys Asp Phe Met
145                 150                 155                 160

Ser Phe Ser Leu Pro Arg Val Phe Ser Gly Leu Ala Asp Ser Lys
                165                 170                 175

Gly Thr Lys Val Gln Met Gly Trp Ser Ile Glu Val Gly Asp Gly Ala
            180                 185                 190

Arg Ala Lys Thr Leu Thr Leu Pro Glu Ala Met Lys Glu Gly Phe Ser
        195                 200                 205

Leu Leu Ile Asp Asn His Arg Met Thr Phe His Val Pro Phe Asn Ala
    210                 215                 220

Thr Gly Val Thr His Tyr Val Gln Gly Asn Ser His Leu Tyr Met Val
225                 230                 235                 240

Ser Leu Lys Leu Thr Phe Ile Ser Pro Gly Gln Lys Val Ile Phe Ser
                245                 250                 255

Ser Gln Ala Ile Cys Ala Pro Asp Pro Val Thr Cys Asn Ala Thr His
            260                 265                 270

Met Thr Leu Thr Ile Pro Glu Phe Pro Gly Lys Leu Lys Ser Val Ser
        275                 280                 285

```
Phe Glu Asn Gln Asn Ile Asp Val Ser Gln Leu His Asp Asn Gly Ile
            290                 295                 300

Asp Leu Glu Ala Thr Asn Gly Met Lys Leu His Phe Ser Lys Thr Leu
305                 310                 315                 320

Leu Lys Thr Lys Leu Ser Glu Lys Cys Leu Leu His Gln Phe Tyr Leu
                325                 330                 335

Ala Ser Leu Lys Leu Thr Phe Leu Leu Arg Pro Glu Thr Val Ser Met
            340                 345                 350

Val Ile Tyr Pro Glu Cys Leu Cys Glu Ser Pro Val Ser Ile Val Thr
                355                 360                 365

Gly Glu Leu Cys Thr Gln Asp Gly Phe Met Asp Val Glu Val Tyr Ser
370                 375                 380

Tyr Gln Thr Gln Pro Ala Leu Asp Leu Gly Thr Leu Arg Val Gly Asn
385                 390                 395                 400

Ser Ser Cys Gln Pro Val Phe Glu Ala Gln Ser Gln Gly Leu Val Arg
                405                 410                 415

Phe His Ile Pro Leu Asn Gly Cys Gly Thr Arg Tyr Lys Phe Glu Asp
            420                 425                 430

Asp Lys Val Val Tyr Glu Asn Glu Ile His Ala Leu Trp Thr Asp Phe
            435                 440                 445

Pro Pro Ser Lys Ile Ser Arg Asp Ser Glu Phe Arg Met Thr Val Lys
450                 455                 460

Cys Ser Tyr Ser Arg Asn Asp Met Leu Leu Asn Ile Asn Val Glu Ser
465                 470                 475                 480

Leu Thr Pro Pro Val Ala Ser Val Lys Leu Gly Pro Phe Thr Leu Ile
                485                 490                 495

Leu Gln Ser Tyr Pro Asp Asn Ser Tyr Gln Gln Pro Tyr Gly Glu Asn
                500                 505                 510

Glu Tyr Pro Leu Val Arg Phe Leu Arg Gln Pro Ile Tyr Met Glu Val
            515                 520                 525

Arg Val Leu Asn Arg Asp Asp Pro Asn Ile Lys Leu Val Leu Asp Asp
            530                 535                 540

Cys Trp Ala Thr Ser Thr Met Asp Pro Asp Ser Phe Pro Gln Trp Asn
545                 550                 555                 560

Val Val Val Asp Gly Cys Ala Tyr Asp Leu Asp Asn Tyr Gln Thr Thr
                565                 570                 575

Phe His Pro Val Gly Ser Ser Val Thr His Pro Asp His Tyr Gln Arg
            580                 585                 590

Phe Asp Met Lys Ala Phe Ala Phe Val Ser Glu Ala His Val Leu Ser
            595                 600                 605

Ser Leu Val Tyr Phe His Cys Ser Ala Leu Ile Cys Asn Arg Leu Ser
            610                 615                 620

Pro Asp Ser Pro Leu Cys Ser Val Thr Cys Pro Val Ser Ser Arg His
625                 630                 635                 640

Arg Arg Ala Thr Gly Ala Thr Glu Ala Glu Lys Met Thr Val Ser Leu
                645                 650                 655

Pro Gly Pro Ile Leu Leu Leu Ser Asp Asp Ser Ser Phe Arg Gly Val
            660                 665                 670

Gly Ser Ser Asp Leu Lys Ala Ser Gly Ser Ser Glu Lys Ser Arg
                675                 680                 685

Ser Glu Thr Gly Glu Glu Val Gly Ser Arg Gly Ala Met Asp Thr Lys
            690                 695                 700

Gly His Lys Thr Ala Gly Asp Val Gly Ser Lys Ala Val Ala Ala Val
705                 710                 715                 720
```

```
Ala Ala Phe Ala Gly Val Val Ala Thr Leu Gly Phe Ile Tyr Tyr Leu
                725                 730                 735

Tyr Glu Lys Arg Thr Val Ser Asn His
            740                 745

<210> SEQ ID NO 3
<211> LENGTH: 424
<212> TYPE: PRT
<213> ORGANISM: human
<220> FEATURE:
<223> OTHER INFORMATION: Zona pellucida protein ZP3

<400> SEQUENCE: 3

Met Glu Leu Ser Tyr Arg Leu Phe Ile Cys Leu Leu Leu Trp Gly Ser
1               5                   10                  15

Thr Glu Leu Cys Tyr Pro Gln Pro Leu Trp Leu Leu Gln Gly Gly Ala
            20                  25                  30

Ser His Pro Glu Thr Ser Val Gln Pro Val Leu Val Glu Cys Gln Glu
        35                  40                  45

Ala Thr Leu Met Val Met Val Ser Lys Asp Leu Phe Gly Thr Gly Lys
    50                  55                  60

Leu Ile Arg Ala Ala Asp Leu Thr Leu Gly Pro Glu Ala Cys Glu Pro
65                  70                  75                  80

Leu Val Ser Met Asp Thr Glu Asp Val Val Arg Phe Glu Val Gly Leu
                85                  90                  95

His Glu Cys Gly Asn Ser Met Gln Val Thr Asp Asp Ala Leu Val Tyr
            100                 105                 110

Ser Thr Phe Leu Leu His Asp Pro Arg Pro Val Gly Asn Leu Ser Ile
        115                 120                 125

Val Arg Thr Asn Arg Ala Glu Ile Pro Ile Glu Cys Arg Tyr Pro Arg
    130                 135                 140

Gln Gly Asn Val Ser Ser Gln Ala Ile Leu Pro Thr Trp Leu Pro Phe
145                 150                 155                 160

Arg Thr Thr Val Phe Ser Glu Glu Lys Leu Thr Phe Ser Leu Arg Leu
                165                 170                 175

Met Glu Glu Asn Trp Asn Ala Glu Lys Arg Ser Pro Thr Phe His Leu
            180                 185                 190

Gly Asp Ala Ala His Leu Gln Ala Glu Ile His Thr Gly Ser His Val
        195                 200                 205

Pro Leu Arg Leu Phe Val Asp His Cys Val Ala Thr Pro Thr Pro Asp
    210                 215                 220

Gln Asn Ala Ser Pro Tyr His Thr Ile Val Asp Phe His Gly Cys Leu
225                 230                 235                 240

Val Asp Gly Leu Thr Asp Ala Ser Ser Ala Phe Lys Val Pro Arg Pro
                245                 250                 255

Gly Pro Asp Thr Leu Gln Phe Thr Val Asp Val Phe His Phe Ala Asn
            260                 265                 270

Asp Ser Arg Asn Met Ile Tyr Ile Thr Cys His Leu Lys Val Thr Leu
        275                 280                 285

Ala Glu Gln Asp Pro Asp Glu Leu Asn Lys Ala Cys Ser Phe Ser Lys
    290                 295                 300

Pro Ser Asn Ser Trp Phe Pro Val Glu Gly Pro Ala Asp Ile Cys Gln
305                 310                 315                 320

Cys Cys Asn Lys Gly Asp Cys Gly Thr Pro Ser His Ser Arg Arg Gln
                325                 330                 335

Pro His Val Met Ser Gln Trp Ser Arg Ser Ala Ser Arg Asn Arg Arg
            340                 345                 350
```

His Val Thr Glu Glu Ala Asp Val Thr Val Gly Pro Leu Ile Phe Leu
            355                 360                 365

Asp Arg Arg Gly Asp His Glu Val Glu Gln Trp Ala Leu Pro Ser Asp
        370                 375                 380

Thr Ser Val Val Leu Leu Gly Val Gly Leu Val Val Val Ser Leu
385                 390                 395                 400

Thr Leu Thr Ala Val Ile Leu Val Leu Thr Arg Arg Cys Arg Thr Ala
                405                 410                 415

Ser His Pro Val Ser Ala Ser Glu
            420

<210> SEQ ID NO 4
<211> LENGTH: 540
<212> TYPE: PRT
<213> ORGANISM: human
<220> FEATURE:
<223> OTHER INFORMATION: Zona pellucida protein ZP4

<400> SEQUENCE: 4

Met Trp Leu Leu Arg Cys Val Leu Leu Cys Val Ser Leu Ser Leu Ala
1               5                   10                  15

Val Ser Gly Gln His Lys Pro Glu Ala Pro Asp Tyr Ser Ser Val Leu
            20                  25                  30

His Cys Gly Pro Trp Ser Phe Gln Phe Ala Val Asn Leu Asn Gln Glu
        35                  40                  45

Ala Thr Ser Pro Pro Val Leu Ile Ala Trp Asp Asn Gln Gly Leu Leu
    50                  55                  60

His Glu Leu Gln Asn Asp Ser Asp Cys Gly Thr Trp Ile Arg Lys Gly
65                  70                  75                  80

Pro Gly Ser Ser Val Val Leu Glu Ala Thr Tyr Ser Ser Cys Tyr Val
                85                  90                  95

Thr Glu Trp Asp Ser His Tyr Ile Met Pro Val Gly Val Glu Gly Ala
            100                 105                 110

Gly Ala Ala Glu His Lys Val Val Thr Glu Arg Lys Leu Leu Lys Cys
        115                 120                 125

Pro Met Asp Leu Leu Ala Arg Asp Ala Pro Asp Thr Asp Trp Cys Asp
    130                 135                 140

Ser Ile Pro Ala Arg Asp Arg Leu Pro Cys Ala Pro Ser Pro Ile Ser
145                 150                 155                 160

Arg Gly Asp Cys Glu Gly Leu Gly Cys Cys Tyr Ser Ser Glu Glu Val
                165                 170                 175

Asn Ser Cys Tyr Tyr Gly Asn Thr Val Thr Leu His Cys Thr Arg Glu
            180                 185                 190

Gly His Phe Ser Ile Ala Val Ser Arg Asn Val Thr Ser Pro Pro Leu
        195                 200                 205

Leu Leu Asp Ser Val Arg Leu Ala Leu Arg Asn Asp Ser Ala Cys Asn
    210                 215                 220

Pro Val Met Ala Thr Gln Ala Phe Val Leu Phe Gln Phe Pro Phe Thr
225                 230                 235                 240

Ser Cys Gly Thr Thr Arg Gln Ile Thr Gly Asp Arg Ala Val Tyr Glu
                245                 250                 255

Asn Glu Leu Val Ala Thr Arg Asp Val Lys Asn Gly Ser Arg Gly Ser
            260                 265                 270

Val Thr Arg Asp Ser Ile Phe Arg Leu His Val Ser Cys Ser Tyr Ser
        275                 280                 285

```
Val Ser Ser Asn Ser Leu Pro Ile Asn Val Gln Val Phe Thr Leu Pro
    290             295             300

Pro Pro Phe Pro Glu Thr Gln Pro Gly Pro Leu Thr Leu Glu Leu Gln
305             310             315                 320

Ile Ala Lys Asp Lys Asn Tyr Gly Ser Tyr Tyr Gly Val Gly Asp Tyr
            325             330                 335

Pro Val Val Lys Leu Leu Arg Asp Pro Ile Tyr Val Glu Val Ser Ile
            340             345             350

Leu His Arg Thr Asp Pro Tyr Leu Gly Leu Leu Leu Gln Gln Cys Trp
        355             360             365

Ala Thr Pro Ser Thr Asp Pro Leu Ser Gln Pro Gln Trp Pro Ile Leu
    370             375             380

Val Lys Gly Cys Pro Tyr Ile Gly Asp Asn Tyr Gln Thr Gln Leu Ile
385             390             395             400

Pro Val Gln Lys Ala Leu Asp Leu Pro Phe Pro Ser His His Gln Arg
            405             410             415

Phe Ser Ile Phe Thr Phe Ser Phe Val Asn Pro Thr Val Glu Lys Gln
            420             425             430

Ala Leu Arg Gly Pro Val His Leu His Cys Ser Val Ser Val Cys Gln
        435             440             445

Pro Ala Glu Thr Pro Ser Cys Val Val Thr Cys Pro Asp Leu Ser Arg
    450             455             460

Arg Arg Asn Phe Asp Asn Ser Ser Gln Asn Thr Thr Ala Ser Val Ser
465             470             475             480

Ser Lys Gly Pro Met Ile Leu Leu Gln Ala Thr Lys Asp Pro Pro Glu
            485             490             495

Lys Leu Arg Val Pro Val Asp Ser Lys Val Leu Trp Val Ala Gly Leu
            500             505             510

Ser Gly Thr Leu Ile Leu Gly Ala Leu Leu Val Ser Tyr Leu Ala Val
        515             520             525

Lys Lys Gln Lys Ser Cys Pro Asp Gln Met Cys Gln
    530             535             540
```

PHARMACEUTICAL COMPOSITION FOR TREATING OR PREVENTING OVARIAN CANCER

FIELD OF THE INVENTION

The present invention relates to the field of therapeutic and prophylactic treatment of ovarian cancer and metastases thereof. More specifically, the invention relates to immunogenic polypeptides comprising at least a portion of an ovarian tissue cell-associated protein or immunologically active variants thereof and to nucleic acids encoding such polypeptides. Such polypeptides and nucleic acid sequences may be used in vaccines and pharmaceutical compositions for therapeutic and prophylactic treatment of ovarian cancer and metastases thereof.

BACKGROUND OF THE INVENTION

Ovarian cancer is the eighth most common type of cancer among women. The American Cancer Society estimates that about 22,220 new cases of ovarian cancer will be diagnosed in the United States during 2005. Ovarian cancer accounts for about 3% of all cancers in women. Because many ovarian cancers cannot be detected early in their development, they account for a disproportionate number of fatal cancers, being responsible for almost half the deaths from cancer of the female genital tract; more deaths than any other reproductive organ cancer. Older women are at higher risk. More than half of the deaths from ovarian cancer occur amongst women between 55 and 74 years of age. About 25% of ovarian cancer deaths occur amongst women between 35 and 54 years of age.

The main treatments for ovarian cancer are surgery, chemotherapy, and radiation therapy. Combinations of these treatments are used to treat ovarian cancer.

Surgery is the usual initial treatment for women diagnosed with ovarian cancer. The ovaries, the fallopian tubes, the uterus, and the cervix are usually removed. Staging during surgery (to find out whether the cancer has spread) generally involves removing lymph nodes, samples of tissue from the diaphragm and other organs in the abdomen, and fluid from the abdomen. If the cancer has spread, the surgeon usually removes as much of the cancer as possible. This reduces the amount of cancer that will have to be treated later with chemotherapy or radiation therapy Chemotherapy is the use of drugs to kill cancer cells. Chemotherapy may be given to destroy any cancerous cells that may remain in the body after surgery, to control tumour growth, or to relieve symptoms of the disease. Most drugs used to treat ovarian cancer are given intravenously or directly into the abdomen through a catheter.

Radiation therapy, also called radiotherapy, involves the use of high-energy rays to kill cancer cells. Radiation therapy affects the cancer cells only in the treated area. The radiation may come from a machine or women receive a treatment called intraperitoneal therapy in which radioactive is put directly into the abdomen through a catheter.

Deciding on a particular course of treatment is typically based on a variety of prognostic parameters and markers [Fitzgibbons, et al. (2000) Arch. Pathol. Lab. Med. 124:966-978; Hamilton and Piccart (2000) Ann. Oncol. 11:647-663)], including genetic predisposition markers BRCA-1 and BRCA-2 [Robson (2000) J. Clin. Oncol. 18:113sup-118sup].

Although many ovarian cancer patients are effectively treated, the current therapies can all induce serious side effects, which diminish quality of life. Moreover, approximately 85% of the patients that have been effectively treated with platinum- and paclitaxel-based chemotherapy, including complete responses, relapse within two years after treatment.

The identification of novel therapeutic targets is essential for improving the current treatment of ovarian cancer patients. Recent advances in molecular medicine have increased the interest in tumour-specific cell surface antigens that could serve as targets for various immunotherapeutic or small molecule strategies.

Among the various elements of the immune system, T lymphocytes are probably the most adept to recognize and eliminate cells expressing foreign or tumour-associated antigens. Cytotoxic T Lymphocytes (CTLs) express the CD8 cell surface marker and are specialized at inducing lysis of the target cells with which they react via the perforin/granzyme and/or the Fas/Fas-L pathways. The T-cell receptor (TCR) for antigen of CTLs binds to a molecular complex on the surface of the target cell formed by small peptides (8-11) residues derived from processed foreign or tumour associated antigens, which associate with major histocompatibility complex (MHC) class I molecules.

The other major T-cell subset, helper T lymphocytes (HTLs or T helper cells), is characterized by the expression of CD4 surface marker. The T helper cells recognize slightly larger peptides (11-20 residues), also derived from foreign or tumour associated antigens, but in the context of MHC class II molecules, which are only expressed by specialized antigen presenting cells (APCs) such as B lymphocytes, macrophages and dendritic cells (DCs).

As a consequence of TCR stimulation of naive CTLs and HTLs by peptide/MHC complexes on APCs, the CTLs mature into effector killer cells capable of lysing (tumour) cells that express the corresponding peptide/MHC class I complex. Activated HTLs amplify CTL responses by making the APCs more effective at stimulating the naive CTLs and by producing lymphokines that stimulate the maturation and proliferation of CTLs. The potentiating effect of T helper cells occurs both in secondary lymphoid organs where the immune response is initiated and at the tumor site where CTL responses need to be sustained until the tumour cells are eliminated. Thus, one would predict that vaccines should stimulate both tumour-reactive CTLs and HTLs to generate effective antitumour immunity.

Antigens suitable for immunotherapeutic cancer strategies should be highly expressed in cancer tissues and ideally not in normal adult tissues. Expression in tissues that are dispensable for life, however, may be acceptable.

A number of antigens suitable for immunotherapeutic strategies in the treatment of ovarian tumors have been described so far, including MUC1, CTs, SP17 and Her2/neu.

Polymorphic epithelial mucin (MUC1) is a transmembrane protein, present at the apical surface of glandular epithelial cells. It is often overexpressed in ovarian cancer (in more than 90% of all ovarian cancers), and typically exhibits an altered glycosylation pattern, resulting in an antigenically distinct molecule. MUC1 is in early clinical trials as a vaccine target [Gilewski, et al. (2000) Clin. Cancer Res. 6:1693-1701; Scholl, et al. (2000) J. Immunother. 23:570-580]. The tumour-expressed protein is often detectable as tumor marker in the circulation [cf. Bon, et al. (1997) Clin. Chem. 43:585-593].

A unique class of differentiation antigens, the cancer/testis (CT) antigens, are not expressed in normal tissues except for testis and, in some cases, placenta. This fact makes CT antigens attractive targets for specific immunotherapy of cancer. The function of the majority of the CT antigens is currently unknown. Tammela et al. [Tamella, et al. (2004) Cancer Immunity 4:10-21] demonstrated that SCP-1, a CT antigen with a known role in gamete development, is expressed in 15% of ovarian cancer cases. It was suggested that because of its restricted expression in normal tissues and its aberrant expression in tumour tissues SCP-1 might serve as a potential target for vaccine therapy in ovarian cancer.

Another potential target for immunotherapy in patients with ovarian carcinoma is the sperm protein 17 (SP17). Sp17 was found to be expressed in the primary tumor cells from 70% of the patients with ovarian carcinoma. The restricted expression of Sp17 in normal tissue makes it an ideal target for tumour vaccine. A recombinant Sp17 protein was used with monocyte-derived dendritic cells and autologous peripheral blood mononuclear cells to generate Sp17 specific cytotoxic T-lymphocytes (CTLs). Human leukocyte antigen (HLA) class II restricted Sp17 specific CTLs were generated successfully from the peripheral blood of three patients with ovarian carcinoma at the time of disease presentation. These CTLs were able to lyse autologous Epstein-Barr virus-transformed lymphoblastoid cells in an Sp17-dependent manner. The CTLs also lysed Sp17-positive autologous tumour cells, suggesting that Sp17 is processed and presented in association with the HLA class I molecules in Sp17-positive tumour cells. [Chiriva et al. (2002) Cancer 94(9):2447-2453]

Human epidermal growth factor receptor 2 (Her2/neu) is an oncogene that is activated by gene amplification with the increased expression of another (normal) gene product. Her2/neu is overexpressed in 20 to 30% of patients with breast and ovarian cancer. Initial studies to develop a peptide based HER-2/neu vaccine were performed in a rat model [Disis et al. (1999) Clinical Cancer Research 5:1289-1297]. No T-cell responses or anti-body responses were observed in animals immunized with intact rat neu protein. By marked contrast, tolerance to rat neu protein in rats, could be circumvented by immunization with a peptide based vaccine. Rats immunized with neu peptides designed for eliciting CD4+ T-cell responses, generated T-cell and antibody responses specific for both the immunizing peptides and the whole protein.

Brossart et al. demonstrated that patients with advanced breast and ovarian cancer could be efficiently vaccinated with autologues dendritic cells (DCs) pulsed with Her2/neu- or MUC1-derived peptides. In 5 out of 10 patients peptide specific CD8+ cytotoxic T lymphocytes could be detected in the peripheral blood. It was reported that MAGE-3- and CEA-peptide-specific CD8+ T cells were observed in one patient treated with MUC-1 peptide-pulsed DCs, and MUC-1 specific T-cells were observed in another patient after vaccination with HER2/neu derived peptides. It was suggested by Brossart et al. [Brossart et al. (2002) Transfus Apher Sci. 27(2):183-186] that this indicated that epitope spreading occurred in these patients upon treatment.

Epitope spreading is a recognized phenomenon of autoimmune responses and is believed to be an exacerbating factor in CD4+ T cell-mediated autoimmune diseases. The phenomenon has been demonstrated in murine relapsing-remitting experimental autoimmune encephaleomyelitis (EAE), Theiler's murine encephalomyelitis virus-induced demyelineating disease and diabetes in the non-obese diabetic (NOD) mouse. A model has been suggested for how epitope spreading in autoimmune diseases mediated by CD4+ T cells occurs. This model is supported by direct evidence that tissue damage, TCR ligation on CD4+ T cells by MHC class II-peptide complexes, CD40-CD40 ligand interactions and CD28-mediated co-stimulation are required for epitope spreading to become manifest. It is thought that an initiating self-antigen or a persistent viral epitope, presented in MHC class II molecules on the surface of professional antigen-presenting cells (APC) residing in the target tissue, causes the activation of CD4+ T cells specific for that antigen. This T cell activation results in chronic inflammation, leading to damage of the target tissue. Tissue debris is subsequently taken up by APC which have up-regulated expression of MHC class II and co-stimulatory molecules in response to inflammatory cytokines. These APC are then capable of activating CD4+ T cells specific for secondary tissue epitopes presented by the APC. The newly activated T cells then aid in destruction of the target tissue.

Due to the requirement for presentation by APC of exogenous antigen, epitope spreading has historically been thought of as a phenomenon unique to CD4+ T cell responses. However, recent data have indicated that cross-priming by APC can participate in the induction of CD8+ cytotoxic T lymphocyte (CTL) responses as well. In particular, bone marrow chimera studies in murine tumour models have shown that tumour-specific CTL are predominately restricted to the MHC of the host rather than that of the tumour, suggesting that indirect presentation by host APC is involved in the generation of tumour-specific CTL. Moreover, there is increasing evidence that a pathway exists whereby exogenous antigen can be presented for eventual peptide loading onto class I MHC molecules. This phenomenon is best described for dendritic cells (DC) and provides a cellular mechanism to explain the process of cross-priming. Collectively, these data suggest that it may be possible for epitope spreading to occur during a class I MHC-restricted CTL response. Because re-presentation of MHC class I-restricted tumour antigens is known to occur, it has been postulated that if tumour-bearing hosts could initiate a CTL response against a single tumour antigen, that following tumor cell damage caused by the CTL, epitope spreading might occur via a mechanism analogous to that described in CD4+ T cell-mediated autoimmune diseases. Unlike during an autoimmune response, however, CTL epitope spreading during an anti-tumour response could be beneficial to the host by possibly allowing for elimination of variant tumor cells that have lost expression of the antigen (antigen negative tumour cells). [Markiewicz et al., (2001) International Immunology 13:625-632].

Markiewicz et al found that immunization with the single tumour peptide P1A followed by tumour rejection led to CTL activity against a P1A$^-$ tumour, indicating that the phenomenon of epitope spreading is not limited to CD4+ T cell responses. The population of CTL included cells recognized the unrelated antigen PIE. Since this epitope was not included in the vaccine and is a mutated peptide not presented in normal tissues, the source of PIE antigen must have been the tumor cell challenge.

Because many patients have ovarian tumours that express neither one of the aforementioned antigens there is a need to uncover additional antigenic targets for immunotherapy to manage localized and metastatic disease. Accordingly, provided herein are molecular targets for immunotherapeutic intervention in ovarian cancers.

The zona pellucida (ZP) forms an extracellular glycoprotein matrix surrounding the developing and ovulated oocyte and the preimplantation embryo and is also detectable in atretic follicles. The ZP induces acrosome reaction on sperm, determines the species specificity for fertilization and prevents polyspermy in mammals. The zona pellucida contains four major glycoproteins, ZP1, ZP2, ZP3 and ZP4. In vitro studies in mice indicate that O-linked oligosaccharide side chains of ZP3 are involved in the primary binding of the sperm to the ZP3, while ZP2 contributes to the subsequent and persistent ZP binding and functions as a secondary sperm receptor.

The ZP glycoproteins have been studied extensively for the development of vaccines for the fertility control of animals and humans. The proposed vaccine action is the induction in female subjects of effective sustained, but reversible levels of ZP-specific antibodies that inhibit sperm-egg binding and/or prevent sperm penetration of the ZP. Passive immunization of female mice with rat monoclonal antibodies against mouse ZP2 or ZP3 resulted in localization of the antibodies to intra-ovarian oocytes and long-lasting but reversible contraception. Active immunization of female mice with ZP3-derived peptides ZP3$^{328-342}$, comprising a B-cell epitope recognized by the ZP3-specific contraceptive antibody, also led to reversible albeit incomplete contraception. These ZP3 peptides also induced a T cell response to the ZP3 peptide. These CD4$^+$ ZP3 specific T cells adoptively transfer autoimmune ovarian disease (AOD) to syngeneic recipients. Since the desired contraceptive effect of ZP3 immunization is known to be mediated by antibodies, an acceptable contraceptive ZP vaccine should induce an adequate antibody response without activation of ZP3-specific T cells. Indeed a chimeric peptide consisting of a foreign T-cell epitope from bovine ribonuclease (RNase) and a minimal and modified murine ZP3$^{335-342}$ B cell epitope has been designed that elicits antibodies to ZP and has a significant contraceptive effect without causing significant oophoritis/AOD. The bovine RNase T-cell epitope stimulates helper T cell (helper T lymphocytes, HTL) responses in mice, thus potentiating the contraceptive effectiveness without inducing ZP(3)-specific T cell action and T-cell mediated ovarian damage.

Immunisation with (self)ZP antigen has also been used to study autoimmune ovarian disease (AOD). More in particular, animal models suitable for studying AOD have been reported wherein autoimmune disease was induced using ZP antigen vaccination. For example, it was demonstrated by Rhim et al. [Rhim et al. (1992) J. Clin. Invest. 89:28-35] that in B6AF$_1$ mice T-cell and antibody response were induced by vaccination with mouse ZP3$^{328-342}$ peptide. Further studies on truncated ZP3$^{328-342}$ peptides substantiated that a T cell response is sufficient for induction of oophoritis; seven of such peptides lacking antibody binding sites, elicited severe oophoritis without concomitant antibody response. These peptides include a minimal oophoritogenic peptide of eight amino acids, ZP3$^{330-337}$, which overlaps the seven amino acid antibody binding site, ZP3$^{336-342}$, by two residues.

It was reported by Bagavant et al. [Bagavant et al. (1999) Biology of Reproduction 61:635-642] that transfer of ZP3 peptide-specific T-cells into naïve recipient mice resulted in granulomatous oophoritis and enhanced ovarian expression of IL-1, TNF-α and IFN-γ. However the ovarian function of cell recipients was normal and the mice remained fertile. Antibody to ZP3 alone does not cause any ovarian pathology. Co-transfer of pathogenic T cells and ZP antibody together targets the inflammation into developing follicles leading to their destruction and the development of ovarian atrophy. In another study Bagavant et al [Bagavant et al. (2002) American Journal of Pathology 160:141-149] demonstrated that ZP3 peptide (human ZP3$^{328-341}$, macaque ZP3$^{328-341}$ and mouse ZP3$^{330-342}$) immunization in primates can elicit a T-cell response and cause ovarian immunopathology that is similar to murine AOD.

International patent application no. WO 2005/026735 (Buschmann et al.) relates to differentially expressed tumour-specific immunogenic membrane proteins and to their uses, in particular for finding at least one therapeutic molecule or compound which specifically regulates the expression of at least one of said membrane proteins, or for finding a therapeutic molecule that specifically binds to and/or interacts with any of said membrane proteins. The membrane protein can be SYPL, STOML2, RAGA, CLNS1A, PRNP, GNB2L1, GNG4, ITM2B, ITM1, TM9SF2, TM4SF6, OPRL1, LRP4, GLEPP1, TLR3 and/or ZP3. WO 2005/026735 teaches to administer the aforementioned therapeutic molecule or compound to neoplastic target cells for modulating proliferation, differentiation and/or cell migration of said neoplastic target cells. It is stated that the non-steroid dependent cancer to be treated results from the aberrant expression and/or biological activity of at least one of said immunogenic membrane proteins. It is also briefly mentioned in WO 2005/026735 that the development of a specific lesion, such as a pro-neoplastic lesion that can be found in epithelial tissues, into a neoplastic lesion can be inhibited by inoculating a subject with one of said membrane proteins adequate to produce antibody and/or T cell immune response. It is further specified that according to another embodiment the method comprises delivering one of the immunogenic membrane proteins via a vector directing expression of the said protein in vivo in order to induce such an immunological response to produce antibody to protect the subject from disease. Thus, WO 2005/026735, teaches several methods of suppressing the expression and/or biological activity of, amongst others, ZP3 membrane proteins in neoplastic target cells in order to modulate proliferation, differentiation and/or migration of said target cells, using either siRNA, receptor antagonists or antibody. WO 2005/026735 only discloses the expression of ZP3 membrane protein in certain colon cancer cells. No other reports of tumour associated expression of any ZP glycoprotein are known.

SUMMARY OF THE INVENTION

The present inventors have surprisingly found that suitable antigens for immunotherapeutic strategies in the therapeutic and prophylactic treatment of ovarian cancer and metastases thereof are provided by the zona pellucida glycoproteins. ZP antigens that can induce a CD8$^+$ and/or CD4$^+$ T cell response as well as nucleic acid sequences encoding said antigens, can suitably be used in said immunotherapeutic strategies.

The ovarian tumour cells in patients responding to the present method, may themselves express ZP glycoproteins in significant amounts, such that they are targeted by the primary immune response. However, without wishing to be bound by theory, it is hypothesized that the present method may also largely depend on the phenomenon of epitope spreading; immunization with zona pellucida antigens induces a T-cell response against cells expressing ZP glycoproteins, subsequent cross-presentation to CD8+ and/or CD4+ T-cells of debris of said ZP-expressing cells which contain secondary epitopes by APCs may evoke cytotoxic/cytolytic T-cell immune responses against epitopes derived from different antigens, i.e. antigens that were not used for vaccination. (Tumor)cells expressing these antigens will be attacked in this 'secondary' immune response. In this respect, the present method may also be viewed at as a method wherein a pathology comparable or similar to autoimmune ovarian disease (AOD) is generated.

WO 01/02000 discloses immunogenic compositions comprising an immunogen derived from a zona pellucida protein for control of animal reproduction, treatment of reproductive diseases and disorders and management of animal behaviour. All methods described and/or suggested in WO 01/02000 are based on the finding that these immunogenic compositions can be used to affect the reproductive system of these animals in such a way as to cause either reversible temporary infertility (immunocontraception) or permanent irreversible infertility (immunosterilisation). It is suggested in WO 01/02000 that in rabbits which are allowed to undergo unrestricted estrus, the method may be suitable to prevent a variety of disorders including neoplasias of the reproductive tract and of the mammary glands in these animals. As is commonly known in the art, excessive estrogen exposure, e.g. resulting from an animal undergoing unrestricted estrus, will contribute to the incidence of certain estrogen sensitive neoplastic diseases of the reproductive tract and the mammary glands. As explained in WO 01/02000, in this regard immunosterilisation and/or immunocontraception could be effective alternatives to ovariohysterectomy in trying to reduce (excessive) estrogen exposure. The most common type of neoplastic disease of the reproductive tract that is sensitive to estrogen exposure is endometrium cancer. Ovarian cancers are in general not sensitive to estrogen exposure.

The present invention relates to methods of treating and/or preventing ovarian tumors in a human comprising immunizing said mammal with a source of a polypeptide comprising a class I MHC- or class II MHC-restricted native zona pellucida T cell epitope or immunologically active variants thereof, as well as to compositions suitable for use in such methods.

The present invention will be described in more detail hereafter.

DETAILED DESCRIPTION OF THE INVENTION

A first aspect of the present invention relates to a method for therapeutic and/or prophylactic treatment of ovarian cancer and metastases thereof in a human by inducing a primary immune response to ZP (glyco)proteins, the method comprising the step of administering to said human a source of a polypeptide, said polypeptide comprising a class I MHC- and/or class II MHC-restricted native zona pellucida T cell epitope that is capable of eliciting a T-cell mediated immune response in vivo or an immunologically active variant thereof. In a particularly preferred embodiment of the invention, the present method is a method for therapeutic treatment.

The naming of the ZP glycoprotein components has been rather inconsistent over the years, employing several criteria, including apparent molecular weight, protein sequence length and sequence identity comparison, which has resulted in a confused nomenclature. Harris et al. [(1994) DNA seq. 96:829-834] proposed a uniform system of nomenclature in which ZP genes were named in order of length of their encoded protein sequence from longest to shortest. Since, under those criteria the mouse ZP genes fell in the order ZP2, then ZP1 and then ZP3, a new system was introduced wherein ZP2 became ZPA, ZP1, became ZPB and ZP3 became ZPC. More recently Hughes et al [(1999) BBA-Gene Structure and Expression 1447:303-306], amongst others, reported that the true human orthologue of the known mouse ZP1 gene is not ZPB, but that there is a distinct human ZP1 gene. It is now generally accepted that there are four distinct (human) ZP glycoprotein families ZP1, ZP2, ZP3 and ZPB [cf. Lefievre et al (2004) Hum. Reprod. 19:1580-1586]. The ZPB glycoprotein according to this nomenclature is now also referred to as ZP4. This nomenclature is for example applied in the Uniprot/SWISSprot, ensEMBL, BLAST (NCBI), SOURCE, SMART, STRING, PSORT2, CDART, UniGene and SOSUI databases, all implemented in the Bioinformatic Harvester (http://harvester.embl.de).

In accordance with this the terms ZP1, ZP2, ZP3 and ZP4 are employed herein to denote the four ZP glycoprotein families, wherein ZP2, ZP3 and ZP4 correspond to ZPA, ZPC and ZPB respectively according to the nomenclature proposed by Harris et al. More in particular, the terms hZP1, hZP2, hZP3 and hZP4 as used herein refer to the (glyco)proteins having polypeptide backbones comprised by sequence protocols SEQ ID NO. 1, SEQ ID NO. 2, SEQ ID NO. 3 and SEQ ID NO. 4, respectively.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The term 'ovarian cancer', as used herein, refers to both primary ovarian tumours as well as metastases of said primary ovarian tumours that may have settled anywhere in the body. The method according to the invention may also be advantageously applied as adjunctive therapy during or following treatment of patients using any of the conventional methods, including for example, oophorectomy, radiation therapy and/or chemotherapy. It is however common knowledge that many of the conventional anti-cancer treatments such as chemotherapy and radiation can be highly immunosuppressive. It will thus be clear to the skilled person that the efficacy of the present method may be lower when following such treatments. The invention provides methods which are suitably employed for treatment of primary ovarian cancer and metastases thereof (therapeutic treatment) as well as for preventing metastases and/or recurrence of ovarian cancer optionally after or in combination with other methods of treatment, such as described herein before, (prophylactic treatment).

For the methods of the invention, the human to be treated is a human female, preferably a, juvenile female, a pre-menopausal female or an early menopausal female. In post-menopausal females most of the follicles will have disappeared from the ovaries. The remaining follicles may not express sufficient amounts of ZP glycoproteins for the primary autoimmune response to develop, such that the present method of treating and/or preventing ovarian cancer through ZP vaccination is less likely to succeed in said post-menopausal females compared to juveniles, pre-menopausal and early menopausal females. It is especially preferred that the female mammal is a juvenile or a pre-menopausal female.

The term "epitope" as used herein refers to a portion of an antigen, typically defined by a peptide, which is capable of eliciting a cellular or humoral immune response when presented in a physiologically relevant context in vivo. A "T cell epitope" refers to a peptide or portion thereof that binds to an MHC molecule and is recognized by T cells when presented in MHC molecules. A T cell epitope is capable of inducing a cell mediated immune response via direct or indirect presentation in heterodimeric membrane MHC molecules. Briefly, MHC molecules preferentially bind particular amino acid residues known as "anchor" residues (K. Falk et al., Nature 351:290-96 (1991)). This characterization permits class I and II MHC recognition epitopes to be identified within any known peptide sequence. In the present context, the term "MHC restricted epitope" is synonymous with T cell epitope. The term "class I MHC restricted epitope", as used herein, refers to peptide sequences recognized by cytotoxic T lymphocytes (also called $CD8^+$ cells or CTLs) in association with class I MHC. The term "class II MHC restricted epitope", as used herein, refers to a peptide recognized by helper T cells (also called $CD4^+$ cells or HTLs). A "B cell epitope" is a portion of an antigen, typically a peptide, capable of binding to an antigen binding site of an immunoglobulin and therefore capable of stimulating a humoral response without presentation in an MHC molecule. As explained herein before the polypeptide useful in the present invention, or the nucleic acid encoding said polypeptide, comprises at least one T cell epitope. The use of polypeptides that also comprise a B cell epitope is however not excluded from the present invention. The present immunogenic polypeptides may also include multiple T cell epitopes and, optionally a B cell epitope. When multiple epitopes are present in a peptide, the epitopes may be oriented in tandem or in a nested or overlapping configuration wherein at least one amino acid residue may be shared by two or more epitopes.

The polypeptide of the invention preferably includes one or more MHC class I binding epitopes. As is generally known by the skilled person, an antigen comprising a single peptide epitope will be useful only for treating a (small) subset of patients who express the MHC allele product that is capable of binding that specific peptide. It has been calculated that, in humans, vaccines containing CTL epitopes restricted by HLA-A1, -A2, -A3, -A24 and -B7 would offer coverage to approximately 80% of individuals of most ethnic backgrounds. Therefore, if the present method is used to treat a human female, it is particularly preferred that the present source of a polypeptide comprises an effective amount of one or more different polypeptides comprising one, more preferably two, most preferably three MHC class I binding native ZP epitopes selected from HLA-A1, HLA-A2, HLA-A3, HLA-A24 and HLA-B7 restricted epitopes; or homologues thereof or one or more nucleic acid sequence encoding said one or more polypeptides or homologues thereof.

According to another embodiment the polypeptide of the invention preferably includes one or more MHC class II binding epitopes. The most frequently found MHC class II allele products in humans include HLA-DR1, -DR3, -DR4 and -DR7. Accordingly, it is preferred that the present source of a polypeptides, comprises an effective amount of one or more different polypeptides, said one or more different polypeptides comprising one, more preferably two and most preferably three MHC class II binding native ZP epitopes selected from HLA-DR1, HLA-DR3, HLA-DR4 and HLA-DR7 restricted epitopes; or homologues thereof or one or more nucleic acid sequence encoding said one or more polypeptides or homologues thereof.

In still another embodiment, the present source of a polypeptide comprises an effective amount of one or more polypeptides, said one or more polypeptides comprising one or more MHC class I binding epitopes and one or more MCH class II binding epitopes, as described here above; homologues thereof or one or more nucleic acid sequence encoding said polypeptides or homologues thereof. Even, more preferably said source comprises an effective amount of one or more different polypeptides that together include essentially all of the MHC class I and MHC class II binding epitopes comprised in one of the native ZP glycoproteins; or homologues of said one or more polypeptides or one or more nucleic acid sequence encoding said polypeptides or homologues thereof.

In one embodiment, the present source of a polypeptide comprises an effective amount of one or more different immunogenic polypeptides, which one or more different polypeptides together comprise at least 50%, more preferably at least 70%, still more preferably at least 80%, still more preferably at least 90% and most preferably at least 95% of the MHC class I and MHC class II restricted binding epitopes comprised in a native ZP glycoprotein; or homologues of said one or more polypeptides or one or more nucleic acid sequences encoding them.

In a preferred embodiment the present source of a polypeptide comprises an effective amount of an immunogenic polypeptide, which polypeptide comprises at least 50%, more preferably at least 70%, still more preferably at least 80%, still more preferably at least 90% and most preferably at least 95% of the complete amino acid backbone of a native ZP glycoprotein; or a homologue of said polypeptide or a nucleic acid sequence encoding said polypeptide or homologue thereof.

In another particularly preferred embodiment, the source of a polypeptide comprises an effective amount of a plurality of different overlapping polypeptide fragments of a native ZP glycoprotein, which different overlapping polypeptide fragments are between 18-60 amino acids in length and which together comprise at least 50%, more preferably at least 70%, still more preferably at least 80%, still more preferably at least 90% and most preferably at least 95% of the complete amino acid backbone of said native ZP glycoproteins; homologues of said polypeptides or one or more nucleic acid sequences encoding said polypeptides or homologues thereof. Typically, the amino acid overlap between the different consecutive 16-80 amino acid polypeptide fragments is at least 7 amino acids, preferably at least 8, more preferably at least 9 and most preferably at least 10 amino acids.

The MHC binding motifs for most common MHC class I and II alleles have been described. These motifs itemize the amino acid residues that serve as MHC binding anchors for specific class I and class II MHC alleles. Sophisticated computer-based algorithms that take into account the MHC binding anchors as well as the amino acids sequence of a peptide are used to predict and quantify the binding affinity of the peptide/MHC interaction. Thus, from the input of the known amino acid sequence of Zona Pellucida (glyco)proteins, these algorithms list all potential T-cell epitopes, each with its corresponding predictive binding score. Commonly known bio-informatics tools for these purposes include HLA_BIND, SYFPEITHI, NetMHC and TEPITOPE 2000 [see references 1-6]. Alternatively, the skilled artesian will be able to determine HTL and CTL binding epitopes experimentally using standard experimentation (Current Protocols in Immunology, Wiley Interscience 2004).

In some cases it has been observed that the same peptide may bind to several MHC I or II allele products. In one embodiment, the use of such 'promiscuous' MHC binding peptides in the present method is particularly preferred.

The present 'source of a polypeptide' that is administered to the human according to the present method, may comprise a protein, a digest of the protein and/or fragments thereof, which may be in a purified form or may be comprised within a crude composition, preferably of biological origin, such as lysates, sonicates or fixates of prokaryotic or eukaryotic cell lines. Alternatively, said source of an immunogenic polypeptide may comprise chemically synthesized (poly)peptides or polypeptides that have been produced enzymatically in vitro, which may be in a purified form or may be comprised within a crude composition. The source of the polypeptide may also be a nucleic acid encoding the polypeptide, from an RNA or DNA template. The RNA or DNA molecules may be 'naked' DNA, preferably comprised in vesicles or liposomes, or may be comprised in a vector. The vector may be any (recombinant) DNA or RNA vector known in the art, and preferably is a plasmid wherein genes encoding latency antigens are operably linked to regulatory sequences conferring expression and translation of the encoded messengers. The vector may also be any DNA or RNA virus, such as but not limited to Adenovirus, Adeno-Associated Virus (AAV), a retrovirus, a lentivirus, modified Vaccinia Ankara virus (MVA) or Fowl Pox virus, or any other viral vector capable of conferring expression of polypeptides comprising latency epitopes to a host. DNA vectors may be non-integrating, such as episomally replicating vectors or may be vectors integrating in the host genome by random integration or by homologous recombination. An example of the construction of plasmids incorporating human ZP2 cDNA, which plasmids could suitably be used in accordance with the present invention can be found in a publication by Martinez et al. [(1996) Journal of Reproduction and Fertility Supplement 50:35-41], which is incorporated herein by reference.

DNA molecules comprising genes encoding the polypeptides according to the current invention, optionally embedded in vectors such as viruses or plasmids, may be integrated in a genome of a host. In a preferred embodiment of the invention, such a host may be a micro-organism. Preferably such a recombinant micro-organism is a *Mycobacterium*, for instance of the species *M. tuberculosis* or *M. bovis* and most preferably *M. bovis Bacillus* Calmette Guerin (BCG), capable of delivering to a host the polypeptides or fragments thereof according to the invention. Recombinant BCG and methods for recombination are known in the art, for instance in WO2004094469. Such a recombinant micro-organism may be formulated as a live recombinant and/or live attenuated vaccine, as for instance in Jacobs et al. 1987, Nature, 327(6122):532-5). The vector may also be comprised in a host of bacterial origin, such as but not limited to live-attenuated and/or recombinant *Shigella* or *Salmonella* bacteria.

In one embodiment, the current invention provides a method for the induction of a primary immune response to native Zona Pellucida glycoproteins in a human female, wherein the method comprises the step of administering to the human a source of a polypeptide, said polypeptide comprising a class I MHC- and/or class II MHC-restricted native zona pellucida T cell epitope or an immunologically active variant thereof, wherein said source of a polypeptide comprises an effective amount of an immunogenic polypeptide selected from Zona Pellucida proteins, homologues thereof, and immunologically active fragments of said proteins and homologues thereof, or a nucleic acid sequence encoding said immunogenic polypeptide. According to a preferred embodiment said Zona Pellucida protein is selected from the group of ZP1 protein, ZP2 protein, ZP3 protein and ZP4 protein, more preferably ZP2 protein and ZP3 protein, most preferably ZP2 protein.

The term 'immunologically active fragments thereof' will generally be understood in the art to refer to a fragment of a polypeptide antigen comprising at least an epitope, which means that the fragment at least comprises 4, 5, 6, 7 or 8 contiguous amino acids from the sequence of the polypeptide antigen. According to the present invention the fragment comprises at least a T cell epitope. Thus an 'immunologically active fragment' according to this invention comprises at least 8, 9, 10, 11, 12, 13, or 14 contiguous amino acids from the sequence of the ZP protein antigen or homologue or analogue thereof. Still more preferably the fragment comprises both a CTL and a T helper epitope. Most preferably however, the fragment is a peptide that requires processing by an antigen presenting cell, i.e. the fragment has a length of at least about 18 amino acids, which 18 amino acids are not necessarily a contiguous sequence from the polypeptide antigen.

The terms 'homologues thereof', as used herein refer to polypeptides which differ from the naturally occurring polypeptide by minor modifications, but which maintain the basic polypeptide and side chain structure of the naturally occurring form. Such changes include, but are not limited to: changes in one or a few amino acid side chains; changes in one or a few amino acids, including deletions (e.g., a truncated version of the peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. As used herein, a homologue or analogue has either enhanced or substantially similar functionality as the naturally occurring polypeptide. Typically, when optimally aligned, such as by the programs GAP or BESTFIT using default parameters, a naturally occurring polypeptide and a homologue thereof share at least a certain percentage of sequence identity. GAP uses the Needleman and Wunsch global alignment algorithm to align two sequences over their entire length, maximizing the number of matches and minimizes the number of gaps. Generally, the GAP default parameters are used, with a gap creation penalty=8 and gap extension penalty=2. For proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752, USA. Alternatively percent similarity or identity may be determined by searching against databases such as FASTA, BLAST, etc.

A homologue herein is understood to comprise an immunogenic polypeptide having at least 70%, preferably at least 80%, more preferably at least 90%, still more preferably at least 95%, still more preferably at least 98% and most preferably at least 99% amino acid sequence identity with the naturally occurring ZP polypeptides mentioned above and is still capable of eliciting at least the immune response obtainable thereby. A homologue or analogue may herein comprise substitutions, insertions, deletions, additional N- or C-terminal amino acids, and/or additional chemical moieties, such as carbohydrates, to increase stability, solubility and immunogenicity.

According to a preferred embodiment of the invention, the present immunogenic polypeptides as defined herein before, are glycosylated. Without wishing to be bound by theory it is hypothesized that by glycosylation of these polypeptides the immunogenicity thereof is increased. Therefore, according to a preferred embodiment, the aforementioned immunogenic polypeptide as defined herein before, is glycosylated, having a carbohydrate content varying from 10-80 wt %, based on the total weight of the glycoprotein or glycosylated polypeptide. More preferably said carbohydrate content ranges from 15-70 wt %, still more preferably from 20-60 wt %. In another embodiment, said glycosylated immunogenic polypeptide comprises a glycosylation pattern that is similar to that of the corresponding zona pellucida glycoprotein (or fragment thereof) of the human that is treated. It is hypothesized that this even further increases the immunogenicity of said polypeptide. Thus, it is preferred that the immunogenic polypeptide comprises a glycosylation pattern that is similar to that of the corresponding (fragment of) human ZP glycoprotein.

According to one particularly preferred embodiment, the source of a polypeptide comprises an effective amount of an immunogenic polypeptide selected from human Zona Pellucida proteins, homologues thereof and immunologically active fragments of these proteins and their homologues, or a nucleic acid sequence encoding said immunogenic polypeptide. Preferably said human Zona Pellucida protein (hZP protein) is selected from the group of hZP1 protein, hZP2 protein, hZP3 protein and hZP4 protein. According to an even more preferred embodiment said protein is selected from the group of hZP2 protein and hZP3 protein, more preferably said protein is hZP2 protein.

According to a particularly preferred embodiment, the present method of immunization comprises the administration of a source of immunogenically active polypeptide fragments, said polypeptide fragments being selected from Zona Pellucida protein fragments and/or homologues thereof as defined herein before, said polypeptide fragments comprising dominant CTL and/or HTL epitopes and which fragments are between 18 and 45 amino acids in length. Peptides having a length between 18 and 45 amino acids have been observed to provide superior immunogenic properties as is described in WO 02/070006. Peptides may advantageously be chemically synthesized and may optionally be (partially) overlapping and/or may also be ligated to other molecules, peptides or proteins. Peptides may also be fused to form synthetic proteins, as in PCT/NL03/00929 and in Welters et al. (Vaccine. 2004 Dec. 2; 23(3):305-11). It may also be advantageous to add to the amino- or carboxy-terminus of the peptide chemical moieties or additional (modified or D-) amino acids in order to increase the stability and/or decrease the biodegradability of the peptide. To improve the immunogenicity/immuno-stimulating moieties may be attached, e.g. by lipidation or glycosylation. To enhance the solubility of the peptide, addition of charged or polar amino acids may be used, in order to enhance solubility and increase stability in vivo.

For immunization purposes the aforementioned immunogenic polypeptides according to the invention may also be fused with proteins such as but not limited to tetanus toxin/toxoid, diphtheria toxin/toxoid or other carrier molecules. The polypeptides according to the invention may also be advantageously fused to heatshock proteins, such as recombinant endogenous (murine) gp96 (GRP94) as a carrier for immunodominant peptides as described in (references: Rapp U K and Kaufmann S H, Int Immunol. 2004 April; 16(4):597-605; Zugel U, Infect Immun. 2001 June; 69(6):4164-7) or fusion proteins with Hsp70 (Triebel et al; WO9954464).

The individual amino acid residues of the present immunogenic (poly)peptides of the invention can be incorporated in the peptide by a peptide bond or peptide bond mimetic. A peptide bond mimetic of the invention includes peptide backbone modifications well known to those skilled in the art. Such modifications include modifications of the amide nitrogen, the α-carbon, amide carbonyl, complete replacement of the amide bond, extensions, deletions or backbone cross-links. See, generally, Spatola, Chemistry and Biochemistry of Amino Acids, Peptides and Proteins, Vol. VII (Weinstein ed., 1983). Several peptide backbone modifications are known, these include, ψ [CH$_2$S], ψ [CH$_2$NH], ψ [CSNH$_2$], ψ [NHCO], ψ [COCH$_2$] and ψ [(E) or (Z) CH=CH]. The nomenclature used above, follows that suggested by Spatola, above. In this context, ψ indicates the absence of an amide bond. The structure that replaces the amide group is specified within the brackets.

Amino acid mimetics may also be incorporated in the polypeptides. An "amino acid mimetic" as used here is a moiety other than a naturally occurring amino acid that conformationally and functionally serves as a substitute for an amino acid in a polypeptide of the present invention. Such a moiety serves as a substitute for an amino acid residue if it does not interfere with the ability of the peptide to elicit an immune response against the native ZP T cell epitopes. Amino acid mimetics may include non-protein amino acids, such as β-, γ-, δ-amino acids, β-, γ-, δ-imino acids (such as piperidine-4-carboxylic acid) as well as many derivatives of L-α-amino acids. A number of suitable amino acid mimetics are known to the skilled artisan, they include cyclohexylalanine, 3-cyclohexylpropionic acid, L-adamantyl alanine, adamantylacetic acid and the like. Peptide mimetics suitable for peptides of the present invention are discussed by Morgan and Gainor, (1989) Ann. Repts. Med. Chem. 24:243-252.

According to a preferred embodiment, the present method comprises the administration of a composition comprising one or more of the present immunogenic polypeptides as defined herein above, and at least one excipient. Excipients are well known in the art of pharmacy and may for instance be found in textbooks such as Remmington's pharmaceutical sciences, Mack Publishing, 1995.

The present method for immunization may further comprise the administration, preferably the co-administration, of at least one adjuvant. Adjuvants may comprise any adjuvant known in the art of vaccination and may be selected using textbooks like Current Protocols in Immunology, Wiley Interscience, 2004.

Adjuvants are herein intended to include any substance or compound that, when used, in combination with an antigen, to immunise a human or an animal, stimulates the immune system, thereby provoking, enhancing or facilitating the immune response against the antigen, preferably without generating a specific immune response to the adjuvant itself. Preferred adjuvants enhance the immune response against a given antigen by at least a factor of 1.5, 2, 2.5, 5, 10 or 20, as compared to the immune response generated against the antigen under the same conditions but in the absence of the adjuvant. Tests for determining the statistical average enhancement of the immune response against a given antigen as produced by an adjuvant in a group of animals or humans over a corresponding control group are available in the art. The adjuvant preferably is capable of enhancing the immune response against at least two different antigens. The adjuvant of the invention will usually be a compound that is foreign to a human, thereby excluding immunostimulatory compounds that are endogenous to humans, such as e.g. interleukins, interferons and other hormones.

A number of adjuvants are well known to one skilled in the art. Suitable adjuvants include e.g. incomplete Freund's adjuvant, alum, aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxy-phosphoryloxy)-ethylamine (CGP 19835A, referred to as MTP-PE), DDA (2 dimethyldioctadecylammonium bromide), polyIC, Poly-A-poly-U, RIBI™, GERBU™, Pam3™, Carbopol™, Specol™, Titermax™, tetanus toxoid, diphtheria toxoid, meningococcal outer membrane proteins, diphtheria protein CRM$_{197}$. Preferred adjuvants comprise a ligand that is recognised by a Toll-like-receptor (TLR) present on antigen presenting cells. Various ligands recognised by TLR's are known in the art and include e.g. lipopeptides (see e.g. WO 04/110486), lipopolysaccharides, peptidoglycans, liopteichoic acids, lipoarabinomannans, lipoproteins (from mycoplasma or spirochetes), double-stranded RNA (poly I:C), unmethylated DNA, flagellin, CpG-containing DNA, and imidazoquinolines, as well derivatives of these ligands having chemical modifications.

The present method for immunization may further comprise the administration, preferably the co-administration, of a CD40 binding molecule in order to enhance a CTL response and thereby enhance the therapeutic effects of the methods and compositions of the invention. The use of CD40 binding molecules is described in WO 99/61065, incorporated herein by reference. The CD40 binding molecule is preferably an antibody or fragment thereof or a CD40 Ligand or a variant thereof, and may be added separately or may be comprised within a composition according to the current invention. For therapeutic applications, the present immunogenic polypeptides or nucleic acid sequences encoding them or the present compositions comprising these polypeptides or nucleic acid sequences encoding them are administered to a patient suffering from an ovarian tumour and possibly metastases thereof or to a patient that has received other methods of treating ovarian tumours, e.g. any of the conventional methods described herein before, in an amount sufficient to induce a primary autoimmune response directed against native ZP glycoproteins and tissue cells expressing ZP glycoproteins. An amount sufficient to accomplish this is defined as a "therapeutically-" or "prophylactically-effective dose". Such effective dosages will depend on a variety of factors including the condition and general state of health of the patient. Thus dosage regimens can be determined and adjusted by trained medical personnel to provide the optimum therapeutic or prophylactic effect.

In the present method the one or more immunogenic polypeptides are typically administered at a dosage of about 1 μg/kg patient body weight or more at least once. Often dosages are greater than 10 μg/kg. According to the present invention the dosages preferably range from 1 μg/kg to 1 mg/kg.

According to one preferred embodiment typical dosage regimens comprise administering a dosage of 1-1000 μg/kg, more preferably 10-500 μg/kg, still more preferably 10-150 μg/kg, once, twice or three times a week for a period of one, two, three, four or five weeks. According to a preferred embodiment 10-100 μg/kg is administered once a week for a period of one or two weeks.

The present method preferably comprises administration of the present immunogenic polypeptides and compositions comprising them via the parenteral or oral route, preferably the parenteral route. In another, particularly preferred embodiment of the invention, the present method comprises vaginal administration of the present immunogenic polypeptides and compositions comprising them.

Another embodiment of the invention comprises ex vivo administration of a composition comprising the present immunogenic peptides to mononuclear cells from the patients blood, particularly DC isolated therefrom. A pharmaceutical to facilitate harvesting of DC can be used, such as Progenipoietin™ (Monsanto, St. Louis, Mo.) or GM-CSF/IL-4. After pulsing the DC with peptides and washing to remove unbound peptides, the DC are reinfused into the patient. In this embodiment, a composition is provided comprising peptide-pulsed DC which present the pulsed peptide epitopes in HLA molecules on their surfaces. Methods of inducing an immune response employing ex vivo peptide-pulsed DC are well known to the skilled person.

Another aspect of the invention relates to a pharmaceutical preparation comprising as the active ingredient the present source of a polypeptide as defined herein before. More particularly pharmaceutical preparation comprises as the active ingredient one or more of the aforementioned immunogenic polypeptides selected from the group of ZP proteins, homologues thereof and fragments of said ZP proteins and homologues thereof, or, alternatively, a gene therapy vector as defined herein above.

According to a first embodiment a pharmaceutical preparation is provided comprising one or more of the immunogenic polypeptides of the invention. The concentration of said polypeptide in the pharmaceutical composition can vary widely, i.e., from less than about 0.1% by weight, usually being at least about 1% by weight to as much as 20% by weight or more.

The composition preferably at least comprises a pharmaceutically acceptable carrier in addition to the active ingredient. The pharmaceutical carrier can be any compatible, non-toxic substance suitable to deliver the immunogenic polypeptides or gene therapy vectors to the patient. For polypeptides, sterile water, alcohol, fats, waxes, and inert solids may be used as the carrier. Pharmaceutically acceptable adjuvants, buffering agents, dispersing agents, and the like, may also be incorporated into the pharmaceutical compositions.

According to a particularly preferred embodiment, the present pharmaceutical composition comprises an adjuvant, as defined in more detail herein before. Adjuvants for incorporation in the present composition are preferably selected from the group of ligands that are recognised by a Toll-like-receptor (TLR) present on antigen presenting cells, including lipopeptides (see e.g. WO 04/110486), lipopolysaccharides, peptidoglycans, liopteichoic acids, lipoarabinomannans, lipoproteins (from mycoplasma or spirochetes), double-stranded RNA (poly I:C), unmethylated DNA, flagellin, CpG-containing DNA, and imidazoquinolines, as well derivatives of these ligands having chemical modifications. The skilled person will be able to determine the exact amounts of anyone of these adjuvants to be incorporated in the present pharmaceutical preparations in order to render them sufficiently immunogenic. According to another preferred embodiment, the present pharmaceutical preparation may comprise one or more additional ingredients that are used to enhance CTL immunity as explained herein before. According to a particularly preferred embodiment the present pharmaceutical preparation comprises a CD40 binding molecule.

Methods of producing pharmaceutical compositions comprising polypeptides are described in U.S. Pat. Nos. 5,789, 543 and 6,207,718. The preferred form depends on the intended mode of administration and therapeutic application.

For gene therapy, vectors, e.g. a plasmid, phagemid, phage, cosmid, virus, retrovirus, episome or transposable element, comprising a nucleic acid sequence encoding an immunogenic polypeptide as defined herein before may be incorporated into pharmaceutical compositions. Gene therapy vectors can be delivered to a subject by, for example, intravenous injection, local administration (see U.S. Pat. No. 5,328,470) or by stereotactic injection (see e.g., Chen et al., *PNAS* 91:3054-3057, 1994). The pharmaceutical composition of the gene therapy vector can include the gene therapy vector in an acceptable diluent, or can include a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The present immunogenic polypeptides are preferably administered parentally. The polypeptides for preparations for parental administration must be sterile. Sterilisation is readily accomplished by filtration through sterile filtration membranes, prior to or following lyophilisation and reconstitution. The parental route for administration of the polypeptide is in accordance with known methods, e.g. injection or infusion by intravenous, intraperitoneal, intramuscular, intra-arterial, subcutaneous or intralesional routes. The polypeptide is administered continuously by infusion or by bolus injection. A typical composition for intravenous infusion could be made up to contain 10 to 50 ml of sterile 0.9%

NaCl or 5% glucose optionally supplemented with a 20% albumin solution and between 10 μg and 50 mg, preferably between 50 μg and 10 mg, of the polypeptide. A typical pharmaceutical composition for intramuscular injection would be made up to contain, for example, 1-10 ml of sterile buffered water and between 10 μg and 50 mg, preferably between 50 μg and 10 mg, of the polypeptide of the present invention. Methods for preparing parenterally administrable compositions are well known in the art and described in more detail in various sources, including, for example, Remington's Pharmaceutical Science (15th ed., Mack Publishing, Easton, Pa., 1980) (incorporated by reference in its entirety for all purposes).

For oral administration, the active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable colour, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain colouring and flavouring to increase patient acceptance.

A variety of vaginal drug delivery systems is known in the art. Suitable systems include creams, foams, tablets, gels, liquid dosage forms, suppositories and pessaries Mucoadhesive gels and hydrogels, comprising weakly crosslinked polymers which are able to swell in contact with water and spread onto the surface of the mucosa, have been used for vaccination with peptides and proteins through the vaginal route previously. The use of microspheres for the vaginal delivery of peptide and protein drugs has also been suggested. More detailed specifications of vaginally administered dosage forms including excipients and actual methods of preparing said dosage forms are known, or will be apparent, to those skilled in this art. For example, Remington's Pharmaceutical Sciences (15th ed., Mack Publishing, Easton, Pa., 1980) is referred to.

The immunogenic polypeptides for use in the present invention can be prepared using recombinant techniques in which a nucleotide sequence encoding the polypeptide of interest is expressed in suitable host cells such as described in Ausubel et al., "Current Protocols in Molecular Biology", Greene Publishing and Wiley-Interscience, New York (1987) and in Sambrook and Russell (2001) "Molecular Cloning: A Laboratory Manual ($3^{rd}$ edition), Cold Spring Harbor Laboratory, Cold Spring Harbor Laboratory Press, New York; both of which are incorporated herein by reference in their entirety. Also see, Kunkel (1985) Proc. Natl. Acad. Sci. 82:488 (describing site directed mutagenesis) and Roberts et al. (1987) Nature 328:731-734 or Wells, J. A., et al. (1985) Gene 34:315 (describing cassette mutagenesis).

An example of the preparation of recombinant human ZPA and ZPB, using baculoviruses can be found in the aforementioned publication by Martinez et al. [(1996) Journal of Reproduction and Fertility Supplement 50:35-41].

Examples of the preparation of recombinant human ZPA and ZPB, using bacteria (*E. coli*), yeast cells (*Pichia pastoris*), insect cells (*Autographa californica* multiple nuclear polyhedrosis virus) and Chinese Hamster ovary cells (CHO) as expression systems are disclosed in a publication by Harris et al. [(1999) Protein Expression and Purification 16:298-307], which is incorporated herein by reference.

An aspect of the invention thus relates to a vector comprising a nucleic acid molecule encoding the present immunogenic polypeptide as defined herein before. Preferably the vector is a replicative vector comprising an origin of replication (or autonomously replication sequence) that ensures multiplication of the vector in a suitable host for the vector. Alternatively the vector is capable of integrating into the host cell's genome, e.g. through homologous recombination or otherwise. A particularly preferred vector is an expression vector wherein a nucleotide sequence encoding a polypeptide as defined above, is operably linked to a promoter capable of directing expression of the coding sequence in a host cell for the vector.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active under most physiological and developmental conditions. An "inducible" promoter is a promoter that is regulated depending on physiological or developmental conditions. A "tissue specific" promoter is only active in specific types of differentiated cells/tissues.

Expression vectors allow the immunogenic polypeptides as defined above to be prepared using recombinant techniques in which a nucleotide sequence encoding the polypeptide of interest is expressed in suitable cells, e.g. cultured cells or cells of a multicellular organism, such as described in Ausubel et al., "Current Protocols in Molecular Biology", Greene Publishing and Wiley-Interscience, New York (1987) and in Sambrook and Russell (2001, supra); both of which are incorporated herein by reference in their entirety. Also see, Kunkel (1985) Proc. Natl. Acad. Sci. 82:488 (describing site directed mutagenesis) and Roberts et al. (1987) Nature 328: 731-734 or Wells, J. A., et al. (1985) Gene 34:315 (describing cassette mutagenesis).

Typically, nucleic acids encoding the desired polypeptides are used in expression vectors. The phrase "expression vector" generally refers to nucleotide sequences that are capable of affecting expression of a gene in hosts compatible with such sequences. These expression vectors typically include at least suitable promoter sequences and optionally, transcription termination signals. Additional factors necessary or helpful in effecting expression can also be used as described herein. DNA encoding a polypeptide is incorporated into DNA constructs capable of introduction into and expression in an in vitro cell culture. Specifically, DNA constructs are suitable for replication in a prokaryotic host, such as bacteria, e.g., *E. coli*, or can be introduced into a cultured mammalian, plant, insect, e.g., Sf9, yeast, fungi or other eukaryotic cell lines.

DNA constructs prepared for introduction into a particular host typically include a replication system recognised by the host, the intended DNA segment encoding the desired polypeptide, and transcriptional and translational initiation and termination regulatory sequences operably linked to the polypeptide-encoding segment. A DNA segment is "operably linked" when it is placed into a functional relationship with another DNA segment. For example, a promoter or enhancer is operably linked to a coding sequence if it stimulates the transcription of the sequence. DNA for a signal sequence is operably linked to DNA encoding a polypeptide if it is expressed as a preprotein that participates in the secretion of the polypeptide. Generally, DNA sequences that are operably linked are contiguous, and, in the case of a signal sequence, both contiguous and in reading phase. However, enhancers need not be contiguous with the coding sequences whose transcription they control. Linking is accomplished by ligation at convenient restriction sites or at adapters or linkers inserted in lieu thereof.

The selection of an appropriate promoter sequence generally depends upon the host cell selected for the expression of the DNA segment. Examples of suitable promoter sequences include prokaryotic, and eukaryotic promoters well known in the art (see, e.g. Sambrook and Russell, 2001, supra). The transcriptional regulatory sequences typically include a heterologous enhancer or promoter that is recognised by the host. The selection of an appropriate promoter depends upon the host, but promoters such as the trp, lac and phage promoters, tRNA promoters and glycolytic enzyme promoters are known and available (see, e.g. Sambrook and Russell, 2001, supra). Expression vectors include the replication system and transcriptional and translational regulatory sequences together with the insertion site for the polypeptide encoding segment can be employed. Examples of workable combinations of cell lines and expression vectors are described in Sambrook and Russell (2001, supra) and in Metzger et al. (1988) Nature 334: 31-36. For example, suitable expression vectors can be expressed in, yeast, e.g. *S. cerevisiae*, e.g., insect cells, e.g., Sf9 cells, mammalian cells, e.g., CHO cells and bacterial cells, e.g., *E. coli*. Since prokaryotes do not possess the organelles necessary for glycosylation, polypeptides produced by prokaryotes will not have carbohydrate side chains. Eukaryotes do have the glycosylation machinery, but yeast cells will give a different glycosylation pattern than mammalian cells. It is therefore preferred to use an expression system which gives the most "natural" glycosylation pattern. Towards this end mammalian cells are most preferred. Cell lines having glycosylation machinery similar to that of a human can be particularly useful, since it is hypothesized that antigens according to the present invention having a glcyocylation pattern similar to that of the corresponding human Zona Pellucida glycopolypeptides may have increased immunogenicity. Suitable cell lines include CHO cells, see, e.g., U.S. Pat. No. 5,272,070 and in particular human ovary or follicle cell lines, cf. WO 99/42581.

In vitro mutagenesis and expression of mutant proteins are described generally in Ausubel et al. (1987, supra) and in Sambrook and Russell (2001, supra). Also see, Kunkel (1985, supra; describing site directed mutagenesis) and Roberts et al. (1987, supra; describing cassette mutagenesis).

Another method for preparing the present immunogenic polypeptides is to employ an in vitro transcription/translation system. DNA encoding a polypeptide is cloned into an expression vector as described supra. The expression vector is then transcribed and translated in vitro. The translation product can be used directly or first purified. Polypeptides resulting from in vitro translation typically do not contain the post-translation modifications present on polypeptides synthesised in vivo, although due to the inherent presence of microsomes some post-translational modification may occur. Methods for synthesis of polypeptides by in vitro translation are described by, for example, Berger & Kimmel, Methods in Enzymology, Volume 152, Guide to Molecular Cloning Techniques, Academic Press, Inc., San Diego, Calif., 1987 (incorporated herein by reference in its entirety).

A further aspect of the invention thus relates to a host comprising a vector as defined above. The host cells may be prokaryotic or eukaryotic host cells as indicated above. The host cell may be a host cell that is suitable for culture in liquid or on solid media. Alternatively, the host cell is a cell that is part of a multicellular organism such as a transgenic plant or animal, preferably a non-human animal.

A further aspect the invention relates to a method for producing the present immunogenic polypeptide as defined above. The method comprises the step of culturing a host cell as defined above under conditions conducive to the expression of the polypeptide. Optionally the method may comprise recovery the polypeptide. The polypeptide may e.g. be recovered from the culture medium by standard protein purification techniques, including a variety of chromatography methods known in the art per se.

Another aspect of the invention relates to a transgenic animal comprising in its somatic and germ cells a vector as defined above. The transgenic animal preferably is a non-human animal. Methods for generating transgenic animals are e.g. described in WO 01/57079 and in the references cited therein. Such transgenic animals may be used in a method for producing a polypeptide as defined above, the method comprising the step of recovering a body fluid from a transgenic animal comprising the vector or a female descendant thereof, wherein the body fluid contains the polypeptide, and, optionally recovery of the polypeptide from the body fluid. Such methods are also described in WO 01/57079 and in the references cited therein. The body fluid containing the polypeptide preferably is blood or more preferably milk.

Yet another aspect of the invention relates to a transgenic plant comprising in its cells a vector as defined above. Methods for generating transgenic plants are e.g. described in U.S. Pat. No. 6,359,196 and in the references cited therein. Such transgenic plants may be used in a method for producing a polypeptide as defined above, the method comprising the step of recovering a part of a transgenic plant comprising in its cells the vector or a part of a descendant of such transgenic plant, whereby the plant part contains the polypeptide, and, optionally recovery of the polypeptide from the plant part. Such methods are also described in U.S. Pat. No. 6,359,196 and in the references cited therein.

The invention is further illustrated in the following examples, which are not intended to limit the scope of the invention in any manner.

EXAMPLES

Example 1

Female transgenic mice, carrying a mouse inhibin alpha-subunit promoter/simian virus T-antigen fusion gene, develop tumors in their ovaries originating from theca cells. These tumors develop with 100% penetrance and metastases. These female mice have normal estrous cycles.

For this study CHO expressed rhZP2 is used which has been prepared using the method described by Harris et al. [(1999) Protein Expression and Purification 16:298-307].

The study is conducted in 40 female transgenic mice before the development of ovarian cancer which occurs at approximately 4 months of age: one group of 20 mice are immunized with the recombinant human zona pellucida 2 protein (rhZP2). Two other groups, each of 10 female mice, comprise the control and sham-treated groups. The mice immunized with rhZP2 develop oophoritis, which is macroscopically visible. At autopsy no tumours are found in the mice vaccinated with rhZP2. All control animals and sham-treated mice develop aggressive ovarian tumors and metastasis is seen in all mice. After autopsy the ovaries are weighed as a measure of tumor load. The control and sham-treated mice develop a huge tumor load involving a 20 to 40-fold increase in ovarian weight. The group immunized with rhZP2 only show a small increase in ovarian weight due to the oophoritis.

Example 2

Female transgenic mice, carrying a mouse inhibin alpha-subunit promoter/simian virus T-antigen fusion gene, develop tumors in their ovaries originating from theca cells. These tumors develop with 100% penetrance and metastases. These female mice have normal estrous cycles.

For this study CHO expressed rhZP2 is used which has been prepared using the method described by Harris et al. [(1999) Protein Expression and Purification 16:298-307].

The study is conducted in 40 female transgenic mice after the development of ovarian cancer which occurs at approximately 4 months of age. All mice suffer from ovarian tumours and metastasis at the start of the study. One group of 20 mice are immunized with the recombinant human zona pellucida 2 protein (rhZP2). Two other groups, each of 10 female mice, comprise the control and sham-treated groups. The mice immunized with rhZP2 develop oophoritis, which is macroscopically visible.

After immunisation the control and sham-treated mice all die from the ovarian tumours and metastasis. At autopsy the mice immunized with rhZP2 show no or small ovarian tumours.

REFERENCES

1. Parker, K. C., M. A. Bednarek, and J. E. Coligan. 1994. Scheme for ranking potential HLA-A2 binding peptides based on independent binding of individual peptide side-chains. J. Immunol. 152:163. HLA_BIND (http://bimas-.cit.nih.gov/molbio/hla_bind/)
2. Rammensee, Friede, Stevanovic, MHC ligands and peptide motifs: 1st listing, Immunogenetics 41, 178-228, 1995; SYFPEITHI (http://www.syfpeithi.de/) and Rammensee, Bachmann, Stevanovic:MHC ligands and peptide motifs. Landes Bioscience 1997 (International distributor—except North America: Springer Verlag GmbH & Co. KG, Tiergartenstr. 17, D-69121 Heidelberg
3. Buus S, Lauemoller S L, Worning P, Kesmir C, Frimurer T, Corbet S, Fomsgaard A, Hilden J, Holm A, Brunak S. Sensitive quantitative predictions of peptide-MHC binding by a 'Query by Committee' artificial neural network approach, in Tissue Antigens., 62:378-84, 2003; NetMHC (http://www.cbs.dtu.dk/services/NetMHC/)
4. Nielsen M, Lundegaard C, Worning P, Lauemoller S L, Lamberth K, Buus S, Brunak S, Lund O., Reliable prediction of T-cell epitopes using neural networks with novel sequence representations. Protein Sci., 12:1007-17, 2003.
5. Improved prediction of MHC class I and class II epitopes using a novel Gibbs sampling approach, Nielsen M, Lundegaard C, Worning P, Hvid C S, Lamberth K, Buus S, Brunak S, Lund O., Bioinformatics, 20(9):1388-97, 2004.
6. Sturniolo, T. et al., Nature Biotechnology 17, 555-562, 1999, Generation of tissue-specific and promiscuous HLA ligand databases using DNA chips and virtual HLA class II matrices; TEPITOPE (http://www.vaccinome.com/pages/597444/).

The invention claimed is:

1. A method for treating a primary ovarian tumor and/or metastases thereof in a female human subject, comprising administering to said subject in need thereof an effective amount of an immunogenic glycoprotein or the polypeptide backbone thereof which glycoprotein is selected from the group consisting of human zona pellucida (ZP) glycoproteins hZP1, hZP2, hZP3, and hZP4, thereby treating said ovarian tumor or metastases.

2. The method according to claim 1, wherein the glycoprotein or polypeptide induces immunity mediated by cytotoxic T lymphocytes (CTL).

3. The method according to claim 1, wherein said immunogenic glycoprotein or polypeptide ishZP2 or hZP3.

4. The method according to claim 1, further comprising administering to said subject at least one adjuvant.

5. The method according to claim 1, wherein the subject is a juvenile female or a pre-menopausal female.

6. The method according to claim 1, wherein the subject has already been treated for, or is at risk for, ovarian tumor recurrence or metastases, wherein the administered polypeptide or glycoprotein prevents said metastases and/or recurrence.

7. The method according to claim 6, wherein the subject has been treated with, or wherein said treating further comprises, oophorectomy, radiation therapy and/or chemotherapy.

8. The method according to claim 4 wherein the adjuvant is co-administered with the glycoprotein or polypeptide.

9. The method according to claim 3 wherein said immunogenic glycoprotein or polypeptide is hZP3.

10. A method of generating or enhancing a CTL response against human ZP glycoprotein hZP1, hZP2, hZP3 or hZP4 in a subject, comprising administering to the subject an immunogenic glycoprotein or the polypeptide chain thereof which glycoprotein is selected, respectively, from the group consisting of hZP1, hZP2, hZP3, and hZP4, in an amount effective to generate or enhance said CTL response.

11. The method according to claim 10 wherein the human ZP glycoprotein or polypeptide chain thereof is hZP3.

* * * * *